United States Patent [19]

Spector et al.

[11] 3,939,211

[45] Feb. 17, 1976

[54] CATALYTIC OXIDATION OF HYDROCARBONS

[75] Inventors: Richard Harvey Spector, S. Brunswick Township; Richard Keith Madison, Murray Hill, both of N.J.

[73] Assignee: American Cyanamid Company, Stamford, Conn.

[22] Filed: July 11, 1974

[21] Appl. No.: 487,848

[52] U.S. Cl.............................................. 260/610 B
[51] Int. Cl.² ...................................... C07C 179/02
[58] Field of Search ......... 260/610 B, 610 R, 610 A

[56] References Cited
UNITED STATES PATENTS 2,757,207   7/1956   Lurand et al.................... 260/610 B Primary Examiner—James O. Thomas, Jr.
Assistant Examiner—W. B. Lone
Attorney, Agent, or Firm—Charles J. Fickey

[57] ABSTRACT

The present invention relates to the manufacture of beta-isopropylnaphthalene hydroperoxide, an intermediate product in the manufacture of beta-naphthol.

10 Claims, No Drawings

CATALYTIC OXIDATION OF HYDROCARBONS

Generally stated, the subject matter of the present invention relates to a process for preparing beta-isopropylnaphthalene hydroperoxide. More particularly, the invention relates to a process for preparing beta-isopropylnaphthalene hydroperoxide by oxidizing beta-isopropylnapthalene, in an alkaline aqueous medium with molecular oxygen in the presence of a heavy metal catalyst.

BACKGROUND OF THE INVENTION

Beta-isopropylnaphthalene hydroperoxide has been prepared in the past by reacting beta-isopropylnaphthalene with molecular oxygen at elevated temperatures. The reaction is usually carried out at temperatures between 90° to 150°C. in the presence of an alkaline material employing beta-isopropylnaphthalene hydroperoxide as an initiator to facilitate and accelerate the oxidation reaction. The process has traditionally avoided the use of catalysts; in particular, heavy metal catalysts. See U.S. Pat. No. 2,776,322, Webster et al.

This process has many inherent disadvantages relative to yield and the time involved in carrying the reaction to completion.

It is a primary object of this invention to provide a new and improved process for preparing beta-isopropylnaphthalene hydroperoxide.

It is another object of the invention to provide a method for preparing beta-isopropylnaphthalene hydroperoxide which results in materially higher yields.

Additional objects and advantages will be set forth in part in the description which follows and in part will be obvious from the description, or may be learned by practice of the invention, the objects and advantages being realized and attained by means of the process and improvements particularly pointed out in the appended claims.

THE INVENTION

To achieve the foregoing objects and in accordance with its purpose, as embodied and broadly described, the present invention relates to a process for preparing beta-isopropylnaphthalene hydroperoxide which comprises intimately contacting with agitation beta-isopropylnaphthalene dispersed in an alkaline, aqueous medium, with molecular oxygen at a temperature of from about 75° to 100°C. in the presence of 25 to 1000 parts per million parts of beta-isopropylnaphthalene of a heavy metal catalyst selected from the group consisting of the nickel$^{II}$ complex of $\alpha,\alpha'$-(ethylenedinitrilo)-di-o-cresol, tris(triphenylphosphine)rhodium (I) chloride and bis(triphenylphosphine)iridium carbonylchloride, separating the aqueous and oil phase that is formed and recovering the beta-isopropylnaphthalene hydroperoxide from the oil phase.

It is to be understood that both the foregoing general description and the following detailed description are exemplary and explanatory and are not restrictive of the invention.

The process of the present invention differs from the prior art in that an initiator is not used with the heavy metal catalyst, and it produces a high conversion of beta-isopropylnaphthalene to beta-isopropylnaphthalene hydroperoxide in a short time. In accordance with this invention, beta-isopropylnaphthalene is oxidized to beta-isopropylnaphthalene hydroperoxide by agitating the beta-isopropylnaphthalene dispersed in an alkaline, aqueous solution in the presence of a heavy metal catalyst while a stream of air or oxygen is simultaneously blown through the reaction mixture at a moderately elevated temperature.

The reaction is carried out until analytical techniques indicate sufficient conversion of the beta-isopropylnaphthalene and yield of the hydroperoxide. The reaction mixture may be worked up to recover the hydroperoxide using standard procedures. The oxidation of alpha-isopropylnaphthalene may similarly be carried out to produce alpha-isopropylnaphthalene hydroperoxide.

The temperature at which the oxidation in the heterogeneous liquid phase is conveniently carried out ranges between 75°C. and the boiling temperature of the water at the operating pressure, preferably the reaction is carried out between 80° and 90°C. at atmospheric pressure. A convenient ratio between the liquid hydrocarbon and the aqueous phase may be 2 volumes of beta-isopropylnaphthalene to 1 to 8 volumes of water. Good results may be obtained by using a ratio of 1 volume of beta-isopropylnaphthalene to 1 to 2 volumes of water.

The bulk of the beta-isopropylnaphthalene hydroperoxide produced dissolves in the oily layer of unreacted beta-isopropylnaphthalene which separates from the aqueous phase on standing and can be removed by decantation. The oily layer may be subjected to subsequent decomposition treatment with acidic substances in order to convert the hydroperoxide into beta-naphthol and acetone in accordance with processes known in the art. The free hydroperoxide may be converted to its alkali metal salt by treatment with a strong aqueous solution of the corresponding alkali metal hydroxide. The free hydroperoxide may be obtained from its alkali metal salts by acidifying a solution or suspension thereof in water with a suitable acid such as carbon dioxide.

A small amount of the hydroperoxide may be recovered from the aqueous layer by acidifying the aqueous layer. However, it is preferable to utilize the aqueous layer for the preparation of further dispersion charges or, when carrying out the process in a continuous manner, recycling it to the oxidation process with fresh beta-isopropylnaphthalene.

The product, beta-isopropylnaphthalene hydroperoxide, is a white solid which has a melting point of 59° to 61°C. when recrystallized from petroleum ether. The starting material, beta-isopropylnaphthalene, is a well-known chemical intermediate. Among the references in the literature to this material are Haworth et al, Journal of the Chemical Society, 32, p 1790, and Price et al, Journal of the American Chemical Society, 60, p 2499. The pure beta-isopropylnaphthalene has been found to possess a boiling point of 147.4°C/24.5 mm and a refractive index $N_D^{20}$=1.5867. Generally, it is preferred to utilize beta-isopropylnaphthalene with a purity of at least 95 percent.

The alkaline materials which can be employed in preparing the alkaline, aqueous dispersion of beta-isopropylnaphthalene are, for instance, alkali metal carbonates such as sodium carbonate and potassium carbonate, alkali metal hydroxides, for instance sodium hydroxide or potassium hydroxide, or tertiary alkali metal phosphates. Sodium bicarbonate may also be used. If desired, additional amounts of alkali may be added during the course of the oxidation reaction. The preferred alkaline medium is a 1 percent w/w aqueous solution of sodium carbonate, although the concentration may range from about 0.1 to about 10 percent w/w sodium carbonate.

The molecular oxygen may be in the form of air or mixtures of oxygen with other inert gases or vapors, wherein the oxygen content is richer than in air, or of pure oxygen. As inert diluents, nitrogen, carbon dioxide, steam or the like may be used.

Oxidation of the beta-isopropylnaphthalene may be carried out batchwise or in a continuous manner. The reaction may be carried out at atmospheric pressure or under pressures higher than atmospheric in the magnitude of about 40 to 100 psi. Since the reaction mixture is a heterogeneous system, suitable agitation is necessary. It is particularly important to bring the air, oxygen or other oxygen-containing gas into intimate contact with the liquid phase and this may be effected by using high speed stirrers, suitable nozzles, spargers or their combinations. A convenient way of combining good agitation with the avoidance of a continuous gas phase is achieved by the use of a long, narrow tube wherein by turbulent flow of the liquid in conjunction with the gas a good distribution of the latter in the liquid is achieved.

The oxidation is carried out in a substantially heterogeneous liquid phase as an oil-in-water or water-in-oil dispersion under conditions using low concentrations of a catalytically active heavy metal compound. The catalysts useful in the present invention are selected from the group consisting of the nickel$^{II}$ complex of $\alpha,\alpha'$-(ethylenedinitrilo)di-o-cresol, tris(triphenylphosphine)rhodium (I) chloride and bis-(triphenylphosphine)iridium carbonylchloride.

In general, high hydroperoxide yields and conversions may be rapidly obtained if the concentration of the catalyst in solution in the oxidation reaction mixture is at any particular instant from about 25 parts to 1000 parts, preferably about 50 parts to 250 parts, per million parts of beta-isopropylnaphthalene being oxidized.

The composition of the reaction product is determined by vapor phase chromatography of the organic material obtained by extracting the reaction mixture with a suitable water-insoluble organic solvent, such as benzene, washing the extract with water, and concentrating the solvent to remove volatile components. The vapor phase chromatography is conducted using a silicone support (SE-30) and standard analytical techniques.

The hydroperoxide product in the reaction mixture may be determined by either vapor phase chromatography or by titration. The hydroperoxide reacts with potassium iodide on boiling in an acidified solution of isopropyl alcohol to liberate iodine. The iodine liberation step must be carried out in essentially anhydrous medium in the presence of glacial acetic acid. After the liberation of the iodine, titration with sodium thiosulfate is carried out in the presence of some water. The percentage of beta-isopropylnaphthalene hydroperoxide thus obtained is confirmed by the percentage obtained by the vapor phase chromatography procedure. The hydroperoxide product may be recovered from the organic phase by slowly adding the latter to a concentrated aqueous solution, 25 to 40 percent, of sodium hydroxide to precipitate the sodium salt of the hydroperoxide. However, the isolation of the hydroperoxide is usually not desirable.

The product obtained according to this invention finds various commercial applications. It is particularly useful for the production of beta-naphthol and is also used for the polymerization of vinyl, vinylidene, and vinylene compounds, being highly useful in the copolymerization of butadiene with styrene or acrylonitrile to form synthetic rubber.

The following examples are provided for illustrative purposes and may include particular features of the invention. However, the examples should not be construed as limiting the invention, many variations of which are possible without departing from the spirit or scope thereof. Unless otherwise indicated all of the amounts set forth in the examples are based on parts by weight.

EXAMPLES 1 – VIII

GENERAL PROCEDURE

To a resin pot equipped with a reflux condenser, gas inlet tube, thermometer, and an efficient stirrer is added 20 ml of a 1 percent aqueous solution of sodium carbonate and 19.6 g (0.117 mole) of beta-isopropylnaphthalene. Oxygen is bubbled into the mixture at the temperature and for the length of time as indicated in Table 1. At the end of this time the heating and oxygen stream are turned off and the reaction mixture is allowed to cool to room temperature and settle. The reaction product is then extracted with benzene and the benzene extract is washed with water and concentrated in vacuo to obtain an oily residue. The composition of the residue is determined by passing it through a vapor phase chromatography column containing a silicone carrier (SE-30) using standard analytical procedures. The temperature of the column is about 100°C initially and it is programmed to rise 8°C/minute. The temperature of the injection port is 275°C.

TABLE 1

| R-7568- | Ex. | Catalyst[1] | Parts Catalyst/ Million Parts IPN[2] | °C. | Hr. | Bubbles of $O_2$/ Minute | Product Composition (Percent by Weight) | | | | | | % Material Balance | % Yield of IPN[6] Hydroperoxide |
|---|---|---|---|---|---|---|---|---|---|---|---|---|---|---|
| | | | | | | | IPN Hydroperoxide | IPN | IPEN[3] | ACN[4] | DMNC[5] | Naphthalene | % Impurities | |
| 90 | I | (a) | 25 | 90 | 24 | 55–60 | 7.41 | 83.55 | — | 0.05 | 0.17 | — | 0.33 | 91.3 | 95.7 |
| 77 | II | (a) | 51 | 90 | 24 | 50 | 43.00 | 44.39 | 0.02 | 0.70 | 3.51 | 0.43 | 9.60 | 97.5 | 81.4 |
| 78 | III | (a) | 51 | 70–75 | 24 | 55–60 | 15.70 | 78.67 | trace | 0.12 | 0.78 | 0.45 | 1.00 | 95.8 | 93.7 |
| 72,75 | IV | (a) | 5105 | 90 | 16 | 100 | 22.4 | 6.80 | 1.9 | 15.60 | 16.60 | 0.80 | 34.20 | 65.8 | 30.1 |
| 116 | V | (b) | 255 | 80–85 | 16 | 75–80 | 37.48 | 45.79 | 0.11 | 1.27 | 8.65 | — | 10.08 | 93.4 | 77.6 |
| 118 | VI | (b) | 51 | 80–85 | 16 | 120–140 | 24.23 | 70.30 | 0.36 | 0.30 | 1.96 | — | 2.60 | 97.1 | 90.0 |
| 124 | VII | (c) | 255 | 80–85 | 16 | 120–140 | 28.07 | 68.32 | 0.02 | 0.33 | 2.88 | 0.22 | — | 100.0 | 90.0 |

TABLE 1-continued

| R-7568- | Ex. | Catalyst[1] | Parts Catalyst/ Million Parts IPN[2] | °C. | Hr. | Bubbles of $O_2$/ Minute | IPN Hydroperoxide | IPN | IPEN[3] | ACN[4] | DMNC[5] | Naphthalene | % Impurities | % Material Balance | % Yield of IPN[6] Hydroperoxide |
|---|---|---|---|---|---|---|---|---|---|---|---|---|---|---|---|
| 64 | VIII | None | — | 90 | 24 | 48 | 0.58 | — | — | — | — | — | — | — | — |

[1]Catalyst (a) is tris(triphenylphosphine)rhodium (I) Chloride, RhCl [ P— ( — 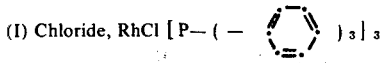 )₃ ]₃

Catalyst (b) is the nickel" complex of α,α'-(ethylenedinitrilo)di-o-cresol,

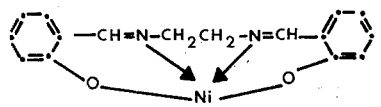

Catalyst (c) is bis(triphenylphosphine)iridium carbonyl chloride, IrCl(CO) [ P— ( 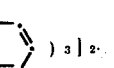 )₃ ]₂.

[2]IPN = 2-isopropylnaphthalene
[3]IPEN = 2-isopropenylnaphthalene
[4]ACN = acetonaphthone
[5]DMNC = dimethyl naphthyl carbinol
[6]Percent yield of IPN Hydroperoxide $$= \frac{\% \text{ IPN Hydroperoxide}}{\% \text{ IPN Hydroperoxide} + \% \text{ Normalized Impurities}} \times 100 \quad \% \text{ Normalized Impurities} = \frac{\% \text{ Impurities}}{\% \text{ Material Balance}} \times 100$$

EXAMPLE IX

To a 2,000-ml baffled glass resin kettle equipped with two turbine blade agitators mounted on a common shaft, a thermometer, condenser, a rotometer and an oxygen sparger is charged 390 ml of beta-isopropylnaphthalene, which had been previously washed twice with 50 percent sodium hydroxide, 390 ml of 1 percent aqueous sodium carbonate, and 19.5 mg of tris-(triphenylphosphine)rhodium (I) chloride. The mixture is stirred slowly initially and the stirring is then increased to 2,200 rpm and the temperature increased to 95°C. over a period of one hour and seventeen minutes. At this point an analysis of the organic layer shows 0.04 percent IPN hydroxide. The temperature is then reduced to 90°C. and the percentage hydroperoxide is determined approximately every hour. The results are shown in Table 2.

TABLE 2

| Time Elapsed (Hr:Min) | Percent IPN Hydroperoxide |
|---|---|
| 0 | 0.04 |
| 1.00 | 0.17 |
| 2.43 | 9.04 |
| 3.58 | 12.80 |
| 4.58 | 16.61 |
| 5.58 | 20.33 |
| 6.58 | 23.09 |
| 7.53 | 25.71 |
| 9.03 | 29.29 |

The data in Table 2 show an average increase in IPN hydroperoxide content of 3.25 percent per hour.

EXAMPLE X

The procedure of Example IX is repeated except that no catalyst is added. The average increase in IPN hydroperoxide content is 1.5 percent per hour.

EXAMPLES XI–XV

The procedure of Examples I-VIII is employed wherein 20 ml of a 1 percent aqueous solution of sodium carbonate and 19.6 g (0.117 mole) of beta-isopropylnaphthalene is stirred and heated at 90°C. for 16 hours in the presence of nickel and cobalt catalysts while bubbling oxygen into the mixture at the rates indicated in Table 3. The reaction mixture is then cooled to room temperature and the hydroperoxide content of the organic layer is determined by titration. The results obtained are shown in Table 3.

The results show that the rates of conversion of beta-isopropylnaphthalene hydroperoxide with these catalysts are significantly lower than the rate obtained with the nickel catalyst of this invention, exemplified by Example XIII.

TABLE 3

| R 7568- | Example | Catalyst[1] | Parts/Catalyst Million Parts IPN | Bubbles of O₂/Minute | Percent IPN-Hydroperoxide |
|---|---|---|---|---|---|
| 172 | XI | (a) | 510 | 90–100 | 0.4 |
| 192 | XII | (b) | 51 | 90–100 | 8.4 |
| 180 | XIII | (c) | 51 | 120–130 | 36.8 |
| 171 | XIV | (d) | 51 | 90–100 | 3.2 |
| 185 | XV | (e) | 51 | 120–130 | 13.4 |

[1] (a) Nickel acetate
(b) Nickel stearate
(c) Ni$^{II}$ complex of $\alpha,\alpha'$-(ethylenedinitrilo)di-o-cresol
(d) Cobalt acetate
(e) Cobalt stearate

What is claimed is:

1. A process for preparing beta-isopropylnaphthalene hydroperoxide which comprises intimately contracting, with agitation beta-isopropylnaphthalene dispersed in an alkaline, aqueous medium with molecular oxygen at a temperature of from about 75° to 100°C. in the presence of 25 to 1000 parts per million parts of beta-isoproplynaphthalene of a heavy metal catalyst selected from the group consisting of the nickel$^{II}$ complex of $\alpha,\alpha'$-(ethylenedinitrilo)di-o-cresol, tris(triphenylphosphine)rhodium (I) chloride and bis(triphenylphosphine) iridium carbonylchloride.

2. The process according to claim 1 wherein the temperature is from about 80° to 90°C.

3. The process according to claim 1 wherein the reaction is carried out under pressure of from about 40 to 100 psi.

4. The process according to claim 1 wherein the catalyst is the nickel$^{II}$ complex of $\alpha,\alpha'$-(ethylenedinitrilo)di-o-cresol.

5. The process according to claim 1 wherein the catalyst is tris(triphenylphosphine)rhodium (I) chloride.

6. The process according to claim 1 wherein the catalyst is bis(triphenylphosphine)iridium carbonylchloride.

7. The process according to claim 1 wherein the concentration of heavy metal catalyst is from about 50 to 250 parts per million of beta-isopropylnaphthalene.

8. The process according to claim 1 wherein the alkaline, aqueous medium is an aqueous solution of sodium carbonate.

9. The process according to claim 8 wherein the concentration of sodium carbonate is from about 0.1 to 10 percent w/w.

10. The process according to Claim 9 wherein the concentration is 1 percent w/w.

* * * * *